United States Patent
Smith et al.

(10) Patent No.: US 8,686,060 B2
(45) Date of Patent: *Apr. 1, 2014

(54) ADHESIVE COMPOSITIONS FOR EASY APPLICATION AND IMPROVED DURABILITY

(75) Inventors: Timothy Michael Smith, Hudson, OH (US); Gary Allan McMaster, Stow, OH (US)

(73) Assignee: Morgan Adhesives Company, Stow, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/546,312

(22) Filed: Jul. 11, 2012

(65) Prior Publication Data

US 2012/0277341 A1    Nov. 1, 2012

Related U.S. Application Data

(63) Continuation-in-part of application No. 12/534,231, filed on Aug. 3, 2009, now Pat. No. 8,242,185.

(51) Int. Cl.

| | |
|---|---|
| C08F 2/50 | (2006.01) |
| C08F 2/46 | (2006.01) |
| B29C 71/04 | (2006.01) |
| A61L 2/08 | (2006.01) |
| A61L 24/00 | (2006.01) |
| C08G 61/04 | (2006.01) |
| C08F 2/48 | (2006.01) |
| A61K 6/083 | (2006.01) |

(52) U.S. Cl.
CPC ... C08F 2/50 (2013.01); C08F 2/48 (2013.01); C03F 7/027 (2013.01); C03F 7/029 (2013.01); A61K 6/083 (2013.01)
USPC ........ 522/64; 522/6; 522/1; 522/71; 522/189; 522/184; 520/1

(58) Field of Classification Search
CPC .............. C08F 2/50; C08F 2/48; C03F 7/027; C03F 7/029; A61K 6/083
USPC ......... 522/35, 905, 114, 129, 117, 121, 64, 6, 522/1, 71, 189, 184; 520/1
See application file for complete search history.

(56) References Cited

U.S. PATENT DOCUMENTS

| | | | |
|---|---|---|---|
| 4,180,599 A | | 12/1979 | Nerath et al. |
| 4,737,559 A | * | 4/1988 | Kellen et al. ................. 526/291 |
| 5,252,694 A | | 10/1993 | Willett et al. |
| 5,264,533 A | * | 11/1993 | Rehmer et al. ................ 526/301 |
| 5,292,842 A | | 3/1994 | Yang |
| 5,462,797 A | | 10/1995 | Williams et al. |
| 5,861,211 A | | 1/1999 | Thakkar et al. |
| 5,955,512 A | | 9/1999 | Numazawa et al. |
| 6,093,757 A | | 7/2000 | Pern |
| 6,204,306 B1 | | 3/2001 | Chabrecek et al. |
| 6,224,949 B1 | | 5/2001 | Wright et al. |
| 6,565,968 B1 | | 5/2003 | Li et al. |
| 6,586,491 B2 | * | 7/2003 | Husemann et al. ............. 522/35 |
| 6,593,490 B1 | | 7/2003 | Li et al. |
| 6,642,298 B2 | | 11/2003 | Foreman et al. |
| 6,670,417 B2 | | 12/2003 | Foreman et al. |
| 6,720,042 B2 | | 4/2004 | Ylitalo et al. |
| 6,756,072 B2 | | 6/2004 | Baumgart et al. |
| 6,866,899 B2 | * | 3/2005 | Wright .......................... 427/516 |
| 6,887,917 B2 | | 5/2005 | Yang et al. |
| 7,521,487 B2 | * | 4/2009 | Hansen et al. ................ 522/178 |
| 7,829,606 B2 | * | 11/2010 | Lu et al. ........................ 522/120 |
| 7,935,424 B2 | | 5/2011 | Maeda et al. |
| 7,964,249 B2 | | 6/2011 | Cartellieri et al. |
| 8,242,185 B2 | * | 8/2012 | Smith et al. .................... 522/31 |
| 2003/0108738 A1 | | 6/2003 | Alahapperuma et al. |
| 2004/0127594 A1 | | 7/2004 | Yang et al. |
| 2005/0072519 A1 | | 4/2005 | Johnson et al. |
| 2006/0069181 A1 | | 3/2006 | Thalacker et al. |
| 2007/0054088 A1 | | 3/2007 | Matijasic et al. |
| 2007/0078246 A1 | | 4/2007 | Herr et al. |
| 2007/0287787 A1 | | 12/2007 | Ferrand |
| 2008/0051485 A1 | | 2/2008 | Frei et al. |
| 2008/0107718 A1 | | 5/2008 | Baron et al. |
| 2010/0108260 A1 | | 5/2010 | Rasche et al. |
| 2010/0120931 A1 | | 5/2010 | Zajaczkowski et al. |
| 2010/0291182 A1 | | 11/2010 | Palasis et al. |

FOREIGN PATENT DOCUMENTS

| | | |
|---|---|---|
| EP | 1381519 A1 | 1/2004 |
| EP | 1639987 | 3/2006 |
| WO | 8403837 A1 | 10/1984 |
| WO | 03099953 A1 | 12/2003 |
| WO | 2008107360 A1 | 9/2008 |

OTHER PUBLICATIONS

Czech, Z, & R. Milker, "Development trends in pressure-sensitive adhesive systems". Materials Science—Poland, pp. 1015-1022, vol. 23, No. 4, 2005.

Dobermann, Andreas & Benno Blickenstorfer, "UV-Curable Hotmelt adhesives for Self-Adhesive Insulation Materials in Automotive Applications". Radtech Report, Mar./Apr. 2006, pp. 19-19.

* cited by examiner

*Primary Examiner* — Ling Choi
*Assistant Examiner* — Jessica E Whiteley
(74) *Attorney, Agent, or Firm* — Tom J. Hall; Cedric M. Richeson

(57) ABSTRACT

The present invention is directed to an adhesive composition comprising a crosslinkable acrylic copolymer, a multi-functionalized crosslinkable oligomer and a photoinitiator wherein the partially cured composition exhibits excellent wet out characteristics as reflected in a tan delta value of at least 0.4, preferably greater than 0.5, more preferable greater than 0.6 as measured at 20° C. resulting from a first curing stage, and the fully cured composition exhibits an improved stiffness and temperature resistance as reflected in a storage elastic modulus of at least 175,000 Pa at 20° C. and a shear adhesion failure temperature of at least 425° F. (218.3° C.) at 1 Kg/in$^2$ (0.155 Kg/cm$^2$), respectively, which result from a second sequential curing stage.

39 Claims, No Drawings

ADHESIVE COMPOSITIONS FOR EASY APPLICATION AND IMPROVED DURABILITY

This is a continuation-in-part application of U.S. patent application Ser. No. 12/534,231, with a filing date of Aug. 3, 2009 which is incorporated herein by reference in its entirety.

TECHNICAL FIELD

This invention relates to adhesive compositions having an improved set of physical properties especially at elevated temperatures yet having low modulus and thus capable of being easily applied.

BACKGROUND OF THE INVENTION

Pressure-sensitive adhesives (PSA) have been known and used for a long time in the art, as they provide many desirable characteristics such as ease of application and a wide range of performance characteristics. Some of the common pressure-sensitive adhesives are formulations based upon acrylates, natural rubbers, synthetic rubbers, vinyl acetates, and silicones. Acrylic PSAs are of particular utility in that they are relatively low in cost, adhere well to a variety of different surfaces, and can be formulated to build adhesion to a surface. Many examples of acrylic pressure sensitive adhesives are described in Pressure Sensitive Adhesives Technology, $1^{st}$ Edition, 1996, Istvan Benedek and Luc J. Heymans, which is incorporated here by reference. An important factor affecting the performance of an acrylic pressure sensitive adhesive is the shear adhesion failure temperature, commonly referred to as SAFT. SAFT defines the upper working temperature of an adhesive and is the upper temperature limit at which the adhesive is able to support a certain amount of weight. However, acrylic PSAs typically have poor high temperature performance. In general, the ease of application of an acrylic pressure-sensitive adhesive relates to the ability of the adhesive to flow or conform to a given substrate with only minimal external force being applied. The greater an adhesive's ability to flow and/or reflow over a surface, the greater its ability to bond to the surface due to higher contact area.

Viscoelastic property characterization of adhesives is an important and most successful rheological tool to study the adhesive's performance. Generally, the viscoelasticity of adhesives is most often determined by dynamic mechanical analysis (DMA). In principle, the adhesion process can be followed easily by using viscoelastic and dynamic mechanical rheological measurements, as the formation of bonds between adhesive and substrate and the flow of an adhesive onto a substrate is reflected in the change of viscoelastic properties. For example, the degree to which the adhesive exhibits more solid-like or liquid-like properties is dependent upon both temperature and time. With dynamic mechanical analysis, a sinusoidal force or stress is applied to an adhesive sample and the resulting sinusoidal deformation or strain is monitored. The sample strain response lags behind the input stress wave with respect to time and this lag is known as the phase angle, $\delta$. The ratio of the dynamic stress to the dynamic strain yields the complex modulus, $G^*$, which can be further broken down to yield the storage (or elastic) modulus, $G'$, and the loss (or viscosity) modulus, $G''$. The storage modulus, $G'$, represents the ability of the adhesive to store energy and it is related to the stiffness of the material. The loss modulus, $G''$ represents the heat dissipated by the adhesive as a result of the material's given molecular motions and this reflects the flow characteristics of the composition. The ratio of the loss and storage moduli provides another useful quantity called tan $\delta$ (tan delta), where tan $\delta=G''/G'$. Tan $\delta$ is associated with the viscoelasticity of the adhesive where a low value (less than 1.0) indicates more solid-like viscoelasticity and a high value (greater than 1.0) reflects more liquid-like viscoelasticity. The values of $G^*$, $G'$ and $G''$ are dependent upon temperature and frequency. Accordingly, the ability of the adhesive to flow at a given temperature will be reflected by its storage and loss moduli and tan $\delta$ values.

What is desired is an adhesive composition having improved resistance to deformation in a shear mode at an elevated temperature, i.e., a high SAFT value, as well as ease of application which is reflected in a tan $\delta$ value of greater than 0.4 as measured a room temperature.

BRIEF SUMMARY OF THE INVENTION

The primary object of the invention is to provide an adhesive composition comprising at least two curing stages, whereby the composition possess excellent wet out characteristics after a first curing stage, and improved stiffness and temperature resistance after a second sequential curing stage.

More particularly, the object of the invention is to provide an adhesive composition having a specific minimum tan delta value resulting from a first curing stage and a specific minimum elastic modulus value and shear adhesion failure temperature value resulting from a second sequential curing stage.

More particularly still, the object of the invention is to provide an adhesive composition having excellent wet out characteristics as reflected in a tan delta value of at least 0.4, preferably greater than 0.5, more preferable greater than 0.6 as measured at 20° C. resulting from a first curing stage, and improved stiffness and temperature resistance as reflected in a storage elastic modulus of at least 175,000 Pa at 20° C. and a shear adhesion failure temperature of at least 425° F. (218.3° C.) at 1 $Kg/in^2$ (0.155 $Kg/cm^2$), respectively, which result from a second sequential curing stage.

The above objects and advantages of the present invention are attained most broadly by an adhesive composition which is free of a mono-functionalized oligomer and encompasses a combination of 1) a crosslinkable acrylic copolymer, 2) a multi-functionalized crosslinkable oligomer, and 3) a photoinitiator which initiates polymerization of the oligomer.

DETAILED DESCRIPTION OF THE INVENTION

Definitions

The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "adhesive" refers to a viscoelastic material which adheres instantaneously to most substrates with the application of slight pressure and remains permanently tacky. An adhesive within the meaning of the term as used herein if it has the properties of a pressure-sensitive adhesive per se or functions as a pressure-sensitive adhesive by admixture with tackifiers, plasticizers or other additives. For more information concerning pressure sensitive adhesives, in general, see for example, Pressure Sensitive Adhesives and Applications, 2$^{nd}$ Ed., by István Benedek (Marcel Dekker 2005) and Handbook of Adhesive Technology, 2$^{nd}$ Ed., edited by A. Pizzi and K. L. Mittal (Marcel Dekker 2003).

A "copolymer" as used herein, refers to polymers formed by the polymerization of reaction of at least two different monomers. For example, the term "copolymer" includes the co-polymerization reaction product of ethylene and an α-olefin, such as 1-hexene. The term "copolymer" is also inclusive of, for example, the co-polymerization of a mixture of ethylene, propylene, 1-propene, 1-butene, 1-hexene, and 1-octene. As used herein, a copolymer identified in terms of a plurality of monomers, e.g., "propylene ethylene copolymer", refers to a copolymer in which either monomer may copolymerize in a higher weight or molar percent than the other monomer or monomers. However, the first listed monomer preferably polymerizes in a higher weight percent than the second listed monomer.

Crosslinkable Acrylic Copolymers

A wide variety of crosslinkable acrylate copolymers can be used and are known in the polymer and adhesive arts, as are methods of preparing the monomers and polymers. Generally, acrylic copolymers are capable of undergoing a crosslinking polymerization reaction with itself or other polymerizable compounds to form a three-dimensional structure and may be further defined as either solvent-borne or solvent-free acrylic copolymers. In preferred embodiments of the invention, the crosslinkable acrylic copolymer is a solvent-borne acrylic copolymer. In other preferred embodiments, the crosslinkable acrylic copolymer is a solvent-free acrylic copolymer. Solvent-borne acrylic copolymers are adhesives in which volatile organic compounds are the major solvent or dispersant. In contrast, solvent-free acrylic copolymers have an absence of any organic solvent in adhesive. In some embodiments of the present invention, acrylate copolymers may include a comonomer selected from the group consisting of acrylamide, acrylonitrile, acrylic acid, alpha-methyl styrene, butyl acrylate, ethyl acrylate, n-butyl acrylate, 2-ethylhexyl acrylate, glycidylmethacrylate, 2-hydroxyethylmethacrylate, hexyl acrylate, hydroxyethyl acrylate, isobornyl acrylate, isobutyl acrylate, isooctyl acrylate, isodecyl acrylate, isononyl acrylate, methacrylic acid, methyl acrylate, methacrylonitrile, n-vinyl caprolactam, nonyl acrylate, caprolactam, propyl acrylate, tert-butyl acrylate, vinyl acetate, vinyl pyrrlidone, styrene, and combinations thereof.

Examples of useful monomers for the acrylate copolymers include, but not exclusively, the following groups:

Group A—acrylic acid esters of an alkyl alcohol (preferably a non-tertiary alcohol), the alcohol containing from 1 to 14 (preferably from 4 to 14) carbon atoms and include, for example, methyl acrylate, ethyl acrylate, n-butyl acrylate, t-butyl acrylate, hexyl acrylate, isooctyl acrylate, 2-ethylhexyl acrylate, isononyl acrylate, isobornyl acrylate, phenoxyethyl acrylate, decyl acrylate, and dodecyl acrylate;

Group B—methacrylic acid esters of an alkyl alcohol (preferably a non-tertiary alcohol), the alcohol containing from 1 to 14 (preferably from 4 to 14) carbon atoms and include, for example, methyl methacrylate, ethyl methacrylate, n-propyl methacrylate, n-butyl methacrylate, isobutyl methacrylate and t-butyl methacrylate;

Group C—(meth)acrylic acid monoesters of polyhydroxy alkyl alcohols such as 1,2-ethanediol, 1,2-propanediol, 1,3-propane diol, the various butyl diols, the various hexanediols, glycerol, such that the resulting esters are referred to as hydroxyalkyl (meth)acrylates;

Group D—multifunctional (meth)acrylate esters such as 1,4-butanediol diacrylate, 1,6-hexanediol diacrylate, glycerol diacrylate, glycerol triacrylate, and neopentyl glycol diacrylate although these monomers are generally not preferred for reactive extrusion or melt blending;

Group E—macromeric (meth)acrylates such as (meth) acrylate-terminated styrene oligomers and (meth)acrylate-terminated polyethers, such as are described in PCT Patent Application WO 84/03837 and European Patent Application EP 140941; and Group F—(meth)acrylic acids and their salts with alkali metals, including, for example, lithium, sodium, and potassium, and their salts with alkaline earth metals, including, for example, magnesium, calcium, strontium, and barium.

In preferred embodiments of the present invention, the crosslinkable acrylate copolymer includes a comonomer comprising ethyl acrylate, 2-ethylhexyl acrylate, methyl acrylate, vinyl acetate and combinations thereof. In other preferred embodiments, the crosslinkable acrylate copolymer is a solvent-borne crosslinkable acrylate copolymer comprising a comonomer which includes 2-ethylhexyl acrylate, methyl acrylate, vinyl acetate and combinations thereof. An example of a commercially available solvent-borne acrylate copolymer suitable for use in the present invention includes Cytec GMS 2480 from Cytec Industries, Inc., West Paterson, N.J., U.S.A. Cytec GMS 2480 acrylic copolymer is also an example of a thermally and chemically-curable solvent-borne adhesive which includes a crosslinking agent comprising aluminum (III) acetylacetonate (AlAcAc).

In still other preferred embodiments, the crosslinkable acrylate copolymer includes a benzophenone-functionalized acrylic copolymer, preferably a benzophenone-functionalized solvent-free acrylic copolymer comprising 2-ethylhexyl acrylate or butyl acrylate comonomer. In still yet other preferred embodiments, the crosslinkable acrylate copolymer is a solvent-free crosslinkable benzophenone-functionalized acrylate copolymer which includes a copolymer comprising 2-ethylhexyl acrylate or butyl acrylate comonomer. Examples of such acrylate copolymers are commercially available solvent-free acrylate copolymers sold under the trademark acResin®, particularly, acResin® A204, A250, A258, A260 and A3532 from BASF Corporation, Charlotte, N.C., U.S.A. These acResin® acrylic copolymers are each an example of a UV radiation-curable solvent-free adhesive having a chemically built-in photoreactive chemical moiety.

Multi-functionalized Crosslinkable Oligomers

A multi-functionalized crosslinkable oligomer referred to herein is an oligomer having two or more chemically functional moieties capable of undergoing a crosslinking polymerization reaction with itself or other polymerizable compounds to form a three-dimensional structure. The "oligomer" portion of multi-functionalized oligomers refers to a polymer-like compound consisting of a finite number of monomer units, in contrast to a polymer which, at least in principle, consists of an unlimited number of monomers. The upper limit of monomer units is typically less than 50, preferably less than 25 and most preferably, less than 10. The term "telomere" is sometimes used synonymously with oligomer. The oligomer may comprise a single molecular structure as the monomer unit or different molecular structures as comonomer units. Examples of typical oligomeric monomer and comonomer units suitable for use in the present invention include, but are not limited to, acrylate, acrylic, epoxy, polyether, polyol, polyester, saturated and unsaturated rubber, polyurethane and combinations thereof. In a preferred embodiment of the present invention, the oligomeric monomer or comonomer unit is polyurethane. The functional moieties of multi-functionalized oligomers may include, for example, di-functional moieties with terminally positioned moieties, one at each end of the oligomer, or tri-functional moieties, typically comprising one grafted moiety within the oligomer chain and two terminally positioned moieties. Multi-functionalized oligomers useful in the adhesive composition may include, but are not limited to, the represented by structures (I), (II) and (III) shown below:

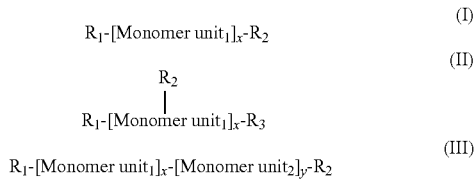

Where $R_1$, $R_2$ and $R_3$ represent functional moieties and may be the same or different functional moiety. In the exemplary structures above, terminal functionalized oligomers are shown in structures (I) and (III), while a terminal and grafted functionalized oligomer is shown in structure (II). Examples of suitable functional moieties include, but not limited to, an acrylate moiety, epoxy moiety, hydroxy moiety and combinations thereof. In one preferred embodiment of the invention, the functional moiety is an acrylate moiety. In another preferred embodiment of the invention, the functional moiety is epoxy or epoxy and hydroxy. As described above, the monomer unit may include one or two or more chemically different repeating units. Examples of commercially available multi-functionalized crosslinkable oligomers include, not are not limited to, urethane multi-acrylate functionalized oligomer, such as, for example, CN9021, CN981, CN820, CN962, CN964, CN965, CN934 and CN972 from Sartomer Company, Inc, Exton, Pa., U.S.A.; and ACTILANE 130, 170, 270, and 290 supplied by Akzo Nobel Resins, Baxley, Ga., U.S.A.; GENOMER 4269 from Rahn U.S.A. Corporation, Aurora, Ill., U.S.A; and Ebecryl 230, 270, 8803, 4827, and 6700 from UCB Chemicals, Smyrna, Ga., U.S.A.

Photoinitiator

A photoinitiator refers to any compound that, by exposure to electromagnetic radiation, undergoes a photoreaction, producing one or more reactive species. These reactive species are capable of initiating the polymerization of reaction of other polymerizable compounds within the composition, and may include, for example, free-radical species and cationic species. In general, most free-radical photoinitiators are reactive to UV radiation having a wavelength between 200 to 400 nm, but some free-radical species have been developed to react to radiation in the IR range. Cationic photoinitiators produce Brönsted or Lewis acid and can be activated by exposure to UV or electron beam radiation. In preferred embodiment of the present invention, a photoinitiator polymerizes the multi-functionalized oligomer. Exemplary photoinitiators useful for polymerizing the functionalized oligomers include acetophenones, aryl phosphineoxides, aryl sulfonium and aryl iodonium salts of hexafluorophosphate, benzyl/benzoins, benzopheneones, thioxanthones, onium salts, and combination thereof. Suitable free radical photoinitiators can include benzoins ethers, such as benzoin methyl ether or benzoin isopropyl ether, substituted benzoin ethers, such as anisoin methyl ether, substituted acetophenones, such as 2,2-diethoxyacetophenone and 2,2-dimethoxy-2-phenylacetophenone, substituted alpha-ketols, such as 2-methyl-2-hydroxypropiophenone, aromatic sulfonyl chlorides, such as 2-naphthalene-sulfonyl chloride, and photoactive oximes, such as 1-phenyl-1,2-propanedione-2(O-ethoxycarbonyl) oxime. Free radical photoinitiators for use in the compositions of the invention include, but are not limited to, commercially available compounds such as Irgacure 651 and 819 from CIBA Specialty Chemicals Corp.; Tarrytown, N.J., U.S.A. An exemplary cationic photoinitiator which is commercially available includes [4-[(2-Hydroxytetradecyl)oxy]phenyl]phenyliodium hexafluoroantimoate from Aldrich Chemical Company, Milwaukee, Wis., U.S.A.

Crosslinking Agent

A crosslinking agent referred to herein is any substance that promotes or regulates intermolecular covalent bonding between acrylic copolymer chains, linking them together to create a more rigid structure. Exemplary crosslinking agents useful for polymerizing acrylic copolymers, particularly, solvent-borne acrylic copolymers include amino resins, aziridines, melamines, isocyanates, metal acid esters, metal chelates, multifunctional propylene imines, and polycarbodiimides. In preferred embodiments of the present invention, the crosslinking agent include metal acid esters comprising aluminum(III) acetylacetonate (AlAcAc), chromium(III) acetylacetonate (CrAcAc), iron(III) acetylacetonate (FeAcAc), cobalt(II) acetylacetonate (CoAcAc), nickel (II) acetylacetonate (NiAcAc), manganese(III) acetylacetonate (MnAcAc), titanium(IV) acetylacetonate (TiAcAc), zinc(II) acetylacetonate (ZnAcAc), zirconium(IV) acetylacetonate (ZrAcAc), and combinations thereof. In a more preferred embodiment, the crosslinking agent is aluminum (III) acetylacetonate (AlAcAc). The crosslinking agent may be added as a separate component during fabrication of the adhesive compositions or may have been previously incorporated into the solvent-borne acrylic copolymer by a supplier of the same.

The term "curing" is typically used as a synonym for crosslinking but can also refer to a combination of additional polymerization reaction plus crosslinking. Curing of crosslinkable adhesive compositions, particularly, acrylic based adhesives may be accomplished generally by thermal, chemical and/or radiation crosslinking techniques. In general, thermal crosslinking includes evaporation or drying of a solvent or dispersant from the adhesive composition. Thermal crosslinking may further include a chemical crosslinking reaction involving the use of one or more crosslinking agents which are activated by the evaporation of solvent from the adhesive composition. For those preferred embodiments employing solvent-borne crosslinkable acrylic copolymers, the acrylic copolymer undergoes thermal and chemical induced crosslinking reactions during a first curing stage by evaporation of a solvent of the adhesive composition. Radiation crosslinking techniques include exposure to electromagnetic radiation of any frequency and preferably include infrared (IR) radiation, visible light, ultraviolet (UV) radiation, X-rays and gamma rays. Radiation crosslinking also includes electron beam radiation methods and exposure to sunlight. For those preferred embodiment employing crosslinkable benzophenone-functionalized acrylic copolymers, particularly, crosslinkable solvent-free benzophenone-functionalized acrylic copolymers, the acrylic copolymer undergoes radiation induced crosslinking reaction during the first curing stage by exposure to UV or electron beam radiation, preferably UV radiation and more preferably UV radiation having a wavelength of less than 300 nm. In all embodiments of the present invention, the crosslinkable multi-functionalized oligomer or oligomers undergo a radiation induced crosslinking reaction during a second curing stage by exposure to UV radiation from a UV bulb or sunlight, preferably, UV radiation having a wavelength of least 200 nm, more preferably by UV radiation having a wavelength of between 300 to 500 nm, and most preferably, by UV radiation having a wavelength of between 320 to 380 nm.

Although specific embodiments of the present invention will now be described with reference to the drawings, it should be understood that such embodiments are by way of example only and merely illustrative of but a small number of the many possible specific embodiments which can represent applications of the principles of the present invention.

EXAMPLES

Examples 1-11

Examples 1-11 are illustrative of adhesive solutions comprising a solvent-borne crosslinkable acrylic copolymer and multi-functionalized crosslinkable oligomer according to the present invention. In a brown reaction vessel was placed an acrylic copolymer in the amounts shown in Table 1a and solvent to provide a mixture having a 43% total solids content. Representative solvents can be organic, and include, for example, acetone, cyclopentanone, 1,2-dimethoxyethane (glyme), ethyl acetate, heptane, hexane, isopropyl alcohol, methylene chloride, methyl-ethyl-ketone, methyl formate, nitromethane, pentanedione, toluene and the like. The multi-functionalized oligomer was then added neat to the acrylic copolymer/solvent mixture in the amounts shown in Table 1a and stirred. Once the oligomer was thoroughly mixed, the photoinitiator was added in the amounts shown in Table 1a along with a sufficient amount of solvent to adjust the mixture to one having a total solids content of 43%.

TABLE 1a

| | Acrylic Copolymer | Multi-Functional Oligomers | | Photoinitiator |
|---|---|---|---|---|
| Example | Cytec 2480 (gram) | CN965 (gram) | CN964 (gram) | Irgacure 819 (gram) |
| 1 | 100 | 4.3 | 0 | 0.43 |
| 2 | 100 | 8.6 | 0 | 0.43 |
| 3 | 100 | 12.9 | 0 | 0.43 |
| 4 | 100 | 17.2 | 0 | 0.43 |
| 5 | 100 | 0 | 4.3 | 0.43 |
| 6 | 100 | 0 | 8.6 | 0.43 |
| 7 | 100 | 0 | 12.9 | 0.43 |
| 8 | 100 | 0 | 17.2 | 0.43 |
| 9 | 100 | 6.45 | 2.15 | 0.43 |
| 10 | 100 | 4.3 | 4.3 | 0.43 |
| 11 | 100 | 2.15 | 6.45 | 0.43 |

Examples 12-19

Examples 12-19 are illustrative of adhesive solutions comprising a crosslinkable benzophenone-functionalized acrylic copolymer and multi-functionalized crosslinkable oligomer according to the present invention. In a brown reaction vessel was placed an acrylic copolymer in the amounts shown in Table 1b. The multi-functionalized oligomer (or oligomers) was then added neat to the acrylic copolymer in the amounts shown in Table 1b and stirred. Once the oligomer was thoroughly mixed, the photoinitiator was added in the amounts shown in Table 1b.

TABLE 1b

| | Acrylic Copolymer BASF acResin ® | Multi-Functional Oligomers | | | Photoinitiator |
|---|---|---|---|---|---|
| Example | A260 (gram) | CN981 (gram) | CN820 (gram) | CN9021 (gram) | Irgacure 819 (gram) |
| 12 | 80 | 0 | 20 | 0 | 0.5 |
| 13 | 80 | 20 | 0 | 0 | 0.5 |
| 14 | 80 | 0 | 10 | 10 | 0.5 |
| 15 | 80 | 10 | 0 | 10 | 0.5 |
| 16 | 70 | 20 | 0 | 10 | 0.5 |
| 17 | 70 | 30 | 0 | 0 | 0.5 |
| 18 | 70 | 0 | 30 | 0 | 0.5 |
| 19 | 70 | 0 | 20 | 10 | 0.5 |

Comparative Examples 1-4

Comparative Examples 1-4 are illustrative of adhesive solutions comprising a solvent-borne acrylic copolymer and a combination of mono-functionalized and multi-functionalized oligomers. Comparative Example 5 is illustrative of adhesive solution comprised solely of a benzophenone-functionalized acrylic copolymer. In a brown reaction vessel were placed the components shown in Table 2 in the same manner as described above for Examples 1-11, except that a combination of a mono-functionalized oligomer and multi-functionalized oligomer was used.

TABLE 2

| | Acrylic Copolymer | | Multi-Functional Oligomers | | Mono-Functional Oligomer | Photoinitiator |
|---|---|---|---|---|---|---|
| | | BASF acResin ® | | | | |
| Comparative Example | Cytec 2480 (gram) | A260 (gram) | CN965 (gram) | CN964 (gram) | Ebecryl CL 1039 (gram) | Irgacure 819 (gram) |
| 1 | 100 | 0 | 4.3 | 0 | 4.3 | 0.43 |
| 2 | 100 | 0 | 6.45 | 0 | 6.45 | 0.43 |
| 3 | 100 | 0 | 0 | 4.3 | 4.3 | 0.43 |
| 4 | 100 | 0 | 0 | 6.45 | 6.45 | 0.43 |
| 5 | 0 | 100 | 0 | 0 | 0 | 0 |

The adhesive solutions described above were coated onto a 90 lb polycoated natural Kraft release liner at a 12 mil wet thickness to yield a 3.5 gram/100 in² dry coating weight. The samples were dried at 23° C. for 10 minutes.

First Curing Stage of Adhesive Compositions

The above prepared coated samples of Examples 1-11 and Comparative Examples 1-4 were dried at 90° C. in a forced air oven for an additional 10 minutes. The samples were removed from the oven and allowed to cool for 5 minutes.

Second Curing Stage of Adhesive Compositions

A 2.0 mil clear Mylar film is laminated to the adhesive surface to form a test specimen for peel, tack and shear testing under Conditions A through D (described below). A silicone coated Mylar film is laminated to the adhesive surface to form a free test specimen for Rheology testing under Conditions E and F (described below). Each specimen was subjected to UV radiation using a Fusion UV D bulb at 15 feet/minute, 300 watts/inch. The Fusion UV D bulb has a range of spectral output between 340 to 440 nm.

Test Conditions

The release liner was removed from the test specimen prior to testing. Test specimens were subjected to the following conditions described below in Table 3 prior to testing.

TABLE 3

| | Conditions |
|---|---|
| A | 1st curing stage was completed before specimen is applied to a test panel for testing with no 2nd curing stage and a 30 minute dwell time before testing. |
| B | 1st curing stage was completed before specimen is applied to a test panel for testing with 2nd curing stage completed after application to the panel and a 30 minute dwell time before testing. |
| C | 1st curing stage was completed before specimen is applied to a test panel with 2nd curing stage was completed after application to the panel and a 24 hour dwell time before testing. |
| D | 1st and 2nd curing stages were completed before specimen is applied to a test panel and 30 minute dwell time before testing. |
| E | 1st curing stage was completed. Specimen was not applied to test panel. |
| F | 1st and 2nd curing stages were completed. Specimen was not applied to test panel. |

Test Methods

180° Peel Force Testing

180° Peel Force measurements were determined as follows: A strip of tape is applied to a standard test panel (stainless steel) with controlled pressure. The tape is peeled from the panel at 180° angle at a rate of 12 inch/minute, during which time the force required to effect peel is measured. The peel force was determined using an Instron tensile tester in accordance with Pressure Sensitive Tape Council (PSTC)-16 Procedure A test method. The results are shown in Table 4.

TABLE 4

| Example | Under Condition A (lb/in) | Under Condition B (lb/in) | Under Condition C (lb/in) | Under Condition D (lb/in) |
|---|---|---|---|---|
| 1 | 4.5 | 4.6 | 4.7 | 4.1 |
| 2 | 5.0 | 4.2 | 5.0 | 3.3 |
| 3 | 4.8 | 4.1 | 4.5 | 2.7 |
| 4 | 5.2 | 3.8 | 4.3 | 3.1 |
| 5 | 4.6 | 4.3 | 5.1 | 4.0 |
| 6 | 5.0 | 4.1 | 4.2 | 2.6 |
| 7 | 5.2 | 3.6 | 3.8 | 2.5 |
| 8 | 5.0 | 3.2 | 3.6 | 2.4 |
| 9 | 4.8 | 3.9 | 4.8 | 3.1 |
| 10 | 4.8 | 3.8 | 4.6 | 3.1 |
| 11 | 4.6 | 3.8 | 4.4 | 2.9 |

TABLE 4-continued

| Example | Under Condition A (lb/in) | Under Condition B (lb/in) | Under Condition C (lb/in) | Under Condition D (lb/in) |
|---|---|---|---|---|
| 12 | 8.4 | 5.0 | — | 4.1 |
| 13 | 5.5 | 3.9 | — | 3.5 |
| 14 | 4.6 | 4.8 | — | 3.6 |
| 15 | 3.5 | 5.3 | — | 3.4 |
| 16 | 4.5 | 4.2 | — | 3.4 |
| 17 | 4.3 | 3.4 | — | 2.9 |
| 18 | 6.5 | 5.0 | — | 5.2 |
| 19 | 6.8 | 5.2 | — | 4.1 |

Loop Tack Testing

Loop Tack measurements were determined as follows: A Mylar test specimen described above was then cut into strips 1 inch wide by 7 inches long. The specimen was brought into contact with a 24 mm×24 mm (one square inch) surface of stainless steel test panel, with the only force applied being the weight of the pressure sensitive article itself. The specimen was then removed from the panel, with the force to remove the adhesive from the adherent measured by a recording instrument. The loop tack was determined using an Instron tensile tester in accordance with Pressure Sensitive Tape Council (PSTC)-16 Procedure A test method. The results are shown in Table 5.

TABLE 5

| Example | Under Condition A (lb/in) | Under Condition D (lb/in) |
|---|---|---|
| 1 | 3.7 | 2.8 |
| 2 | 3.4 | 2.2 |
| 3 | 4.1 | 1.7 |
| 4 | 4.7 | 1.2 |
| 5 | 3.0 | 2.0 |
| 6 | 4.4 | 1.8 |
| 7 | 5.6 | 1.2 |
| 8 | 5.1 | 0.6 |
| 9 | 3.0 | 1.6 |
| 10 | 3.5 | 1.3 |
| 11 | 3.5 | 1.1 |
| 12 | 5.9 | 4.0 |
| 13 | 5.4 | 3.0 |
| 14 | 12.4 | 4.1 |
| 15 | 12.4 | 3.1 |
| 16 | 5.9 | 2.7 |
| 17 | 4.8 | 3.0 |
| 18 | 3.8 | 3.9 |
| 19 | 8.3 | 4.5 |

Shear Adhesion Failure Temperature Testing

Shear Adhesion Failure Temperatures were determined as follows: A Mylar test specimen described above was then cut into strips 1 inch wide by 7 inches long. One end of the specimen was mounted onto stainless steel test panel with a total contact area of one square inch. A 1 kilogram weight attached to the opposite end of the specimen. The specimen was heated to a temperature of 100° F. (38° C.) and allowed to equilibrate for 20 minutes at this temperature. The temperature of the specimen was increased at a rate of 0.5°/min to a maximum temperature of 425° F. (218° C.). The temperature at which the specimen becomes detached from the test panel was recorded. The Shear Adhesion Failure temperature was determined in accordance with Pressure Sensitive Tape Council (PSTC)-101 test method. The results are shown in Table 6.

TABLE 6

| Example | Under Condition C (degrees F.) |
|---|---|
| 1 | >425 |
| 2 | >425 |
| 3 | >425 |
| 4 | >425 |
| 5 | >425 |
| 6 | >425 |
| 7 | >425 |
| 8 | >425 |
| 9 | >425 |
| 10 | >425 |
| 11 | >425 |
| 12 | >425 |
| 13 | >425 |
| 14 | >425 |
| 15 | >425 |
| 16 | >425 |
| 17 | >425 |
| 18 | 403.0 |
| 19 | >425 |
| Comparative Example | |
| 1 | 380 |
| 2 | 323 |
| 3 | 343 |
| 4 | 358 |
| 5 | 149.5 |

Heated Shear Testing

Heated Shear was determined identically as described above for Shear Adhesion Failure Temperature, except that the specimen was heated to a temperature of 320° F. (160° C.) and the amount of time to failure, i.e., where specimen becomes detached from the test panel, was recorded. If no failure was observed, testing was stopped after 10,000 minutes. Heated Shear was determined in accordance with Pressure Sensitive Tape Council (PSTC)-107 Procedure G test method. The results are shown in Table 7.

TABLE 7

| Example | Under Condition C (min) |
|---|---|
| 1 | >10,000 |
| 2 | >10,000 |
| 3 | >10,000 |
| 4 | >10,000 |
| 5 | >10,000 |
| 6 | >10,000 |
| 7 | >10,000 |
| 8 | >10,000 |
| 9 | >10,000 |
| 10 | >10,000 |
| 11 | >10,000 |
| 12 | >10,000 |
| 13 | >10,000 |
| 14 | >10,000 |
| 15 | >10,000 |
| 16 | >10,000 |
| 17 | >10,000 |
| 18 | 245 |
| 19 | >10,000 |
| Comparative Example | |
| 5 | 214 |

Room Temperature Shear Testing

Room Temperature Shear was determined identically as described above for Shear Adhesion Failure Temperature, except that a 2.3 kilogram (5 pound) weight was attached to the un-mounted end of the specimen and the specimen was heated to a temperature of 72° F. (22° C.). For Examples 12-19 and Comparative Example 5, a 4.5 kilogram (10 pound) weight was attached to the un-mounted end of each specimen and the specimen was heated to a temperature of 72° F. (22° C.). The amount of time to failure, i.e., where specimen becomes detached from the test panel, was recorded. If no failure was observed, testing was stopped after 500 hours. Room temperature shear was determined in accordance with Pressure Sensitive Tape Council (PSTC)-107 Procedure G test method. Room Temperature Shear was determined in accordance with Pressure Sensitive Tape Council (PSTC)-107 Procedure A test method. The results are shown in Table 8.

TABLE 8

| Example | Under Condition C (hours) |
|---|---|
| 1 | >500 |
| 2 | >500 |
| 3 | >500 |
| 4 | >500 |
| 5 | >500 |
| 6 | >500 |
| 7 | >500 |
| 8 | >500 |
| 9 | >500 |
| 10 | >500 |
| 11 | >500 |
| 12 | >200 |
| 13 | >200 |
| 14 | 2.9 |
| 15 | 5.7 |
| 16 | 35.0 |
| 17 | >200 |
| 18 | >200 |
| 19 | >200 |
| Comparative Example | |
| 5 | 4.8 |

DMA (Rheology) Testing

Rheology measurements were determined as follows: The specimen is secured to a dynamic mechanical analyzer, Model RDA III supplied by TA Instruments, New Castle, Del., U.S.A. Specifically, the specimen is placed on the bottom plate parallel plate rheometer having a thickness of 1.5 mm and 8 mm diameter and equilibrated at 20° C. The top plate is pressed onto the specimen forming about a 1 mm gap. The specimen is heated to a maximum temperature of 70° C. and at a rate of 3°/min. Various measurements such as the storage modulus (or elastic modulus), G'; the loss modulus, G"; the complex modulus, G*, [the square root of the sum of (G').sup.2+(G").sup.2]; and the δ (tan delta), (ratio of the loss modulus divided by the storage modulus), and complex viscosity were recorded or calculated as function of time as the material sets. A temperature sweep at 10 radians/seconds and a strain of 0.1% were employed for the purpose of measuring the flow properties of the material in its molten state. The results are shown in Tables 9-11.

TABLE 9

| | Under Condition E | | Under Condition F | |
|---|---|---|---|---|
| | Elastic Modulus at 20° C. (kPa) | Elastic Modulus at 70° C. (kPa) | Elastic Modulus at 20° C. (kPa) | Elastic Modulus at 70° C. (kPa) |
| Example | | | | |
| 1 | 145 | 30 | 280 | 53 |
| 2 | 116 | 27 | 405 | 75 |
| 3 | 92 | 25 | 417 | 83 |
| 4 | 70 | 19 | 628 | 115 |
| 5 | 166 | 32 | 334 | 55 |
| 6 | 138 | 27 | 579 | 81 |
| 7 | 107 | 25 | 739 | 98 |
| 8 | 88 | 20 | 1161 | 132 |
| 9 | 119 | 28 | 368 | 70 |
| 10 | 120 | 28 | 417 | 71 |
| 11 | 125 | 28 | 489 | 81 |
| 12 | 116 | 18 | 296 | 42 |
| 13 | 504 | 50 | 910 | 77 |
| 14 | 67 | 10 | 182 | 38 |
| 15 | 99 | 14 | 175 | 48 |
| 16 | 309 | 46 | 343 | 78 |
| 17 | 159 | 90 | 2156 | 133 |
| 18 | 225 | 21 | 449 | 52 |
| 19 | 102 | 12 | 184 | 30 |
| Comparative Example | | | | |
| 1 | 83 | 24 | 344 | 57 |
| 2 | 65 | 20 | 491 | 74 |
| 3 | 95 | 23 | 438 | 59 |
| 4 | 71 | 20 | 663 | 82 |
| 5 | 108 | 27 | — | — |

TABLE 10

| | Under Condition E | | Under Condition F | |
|---|---|---|---|---|
| | Tan delta at 20° C. | Tan delta at 70° C. | Tan delta at 20° C. | Tan delta at 70° C. |
| Example | | | | |
| 1 | 0.88 | 0.50 | 0.77 | 0.47 |
| 2 | 0.87 | 0.45 | 0.71 | 0.42 |
| 3 | 0.86 | 0.42 | 0.70 | 0.41 |
| 4 | 0.99 | 0.40 | 0.68 | 0.40 |
| 5 | 0.80 | 0.48 | 0.75 | 0.44 |
| 6 | 0.95 | 0.49 | 0.76 | 0.45 |
| 7 | 1.03 | 0.44 | 0.69 | 0.41 |
| 8 | 1.20 | 0.43 | 0.64 | 0.39 |
| 9 | 0.80 | 0.45 | 0.69 | 0.41 |
| 10 | 0.93 | 0.45 | 0.70 | 0.43 |
| 11 | 0.92 | 0.45 | 0.67 | 0.40 |
| 12 | 0.81 | 1.52 | 0.76 | 0.66 |
| 13 | 0.71 | 0.57 | 0.57 | 0.42 |
| 14 | 0.79 | 1.67 | 0.60 | 0.57 |
| 15 | 0.73 | 1.25 | 0.50 | 0.43 |
| 16 | 0.63 | 0.53 | 0.54 | 0.37 |
| 17 | 0.67 | 0.40 | 0.58 | 0.33 |
| 18 | 0.85 | 1.12 | 0.82 | 0.64 |
| 19 | 0.80 | 1.38 | 0.70 | 0.69 |
| Comparative Example | | | | |
| 1 | 0.69 | 0.48 | 0.87 | 0.44 |
| 2 | 0.66 | 0.46 | 0.83 | 0.39 |
| 3 | 0.70 | 0.50 | 0.84 | 0.42 |
| 4 | 0.70 | 0.49 | 0.89 | 0.36 |
| 5 | 0.57 | 0.63 | — | — |

TABLE 11

| Example | Complex Viscosity Under Condition E (kPa) |
|---|---|
| 1 | 20500 |
| 2 | 14000 |
| 3 | 12000 |
| 4 | 9600 |
| 5 | 20600 |
| 6 | 19000 |
| 7 | 15000 |
| 8 | 14000 |
| 9 | 14000 |
| 10 | 16000 |
| 11 | 17000 |
| Comparative Example | |
| 1 | 10000 |
| 2 | 7300 |
| 3 | 11500 |
| 4 | 8600 |

It will be apparent to those skilled in the art that modifications and additions can be made to the various embodiments described above, without departing from the true scope and spirit of the present invention. It should be understood that this invention is not intended to be unduly limited by the illustrative embodiments set forth herein and that such embodiments are presented by way of example only with the scope of the invention intended to be limited only by the claims set forth herein as follows.

What is claimed is:

1. A fully cured crosslinked adhesive composition comprising:
   (a) a benzophenone-functionalized crosslinked acrylic copolymer; and
   (b) a multi-functionalized crosslinked oligomer having a functional moiety selected from the group consisting of acrylate, epoxy, hydroxy, and combinations thereof;
   wherein the composition is free of a mono-functionalized oligomer and:
   (i) the acrylic copolymer is crosslinked with itself, and
   (ii) the oligomer is crosslinked with itself, and the fully cured composition has a storage modulus value of at least 175,000 Pa at 20° C., a shear adhesion failure temperature of at least 425° F. (218.3° C.) at 1 Kg/in$^2$ (0.155 Kg/cm$^2$), a heated shear value at 160° C. of greater than 10,000 minutes and a peel force value of at least 3.2 lb./in.

2. The composition as defined in claim 1 wherein the acrylic copolymer is a solvent-free benzophenone-functionalized acrylic copolymer.

3. The composition as defined in claim 1 wherein the acrylic copolymer is polymerized from 2-ethylhexyl acrylate or butyl acrylate.

4. The composition as defined in claim 1 wherein the acrylic copolymer is crosslinked by exposure to light having a wavelength substantially less than 300 nm.

5. The composition as defined in claim 1 wherein the oligomer comprises a urethane oligomer having an acrylate functional moiety.

6. The composition as defined in claim 1 wherein the oligomer is present in an amount of at least 10% by weight relative to the dry weight of the acrylic copolymer.

7. The composition as defined in claim 1 wherein the oligomer is crosslinked by exposure to light having a wavelength substantially greater than 300 nm.

8. The composition as defined in claim 1 wherein the oligomer is crosslinked by exposure to light having a wavelength of between 320 to 440 nm.

9. The composition as defined in claim 1 wherein the fully cured composition has a tan delta value of less than 0.8 as measured at 20° C.

10. The composition as defined in claim 1 wherein the fully cured composition has a room temperature shear adhesion value of least 200 hours at 10 lb./in$^2$ (4.5 Kg/cm$^2$).

11. The composition as defined in claim 1 wherein the fully cured composition has a visible light transmission of between 80 to 100%.

12. A fully cured adhesive composition comprising:
(a) a solvent-free benzophenone-functionalized crosslinked acrylic copolymer which is polymerized from 2-ethylhexyl acrylate or butyl acrylate;
a multi-functionalized crosslinked urethane oligomer having an acrylate functional moiety; wherein the oligomer is present in an amount of at least 10% by weight relative to the dry weight of the acrylic copolymer;
and wherein the composition is free of a mono-functionalized oligomer and:
(i) the acrylic copolymer is crosslinked with itself, and
(ii) the oligomer is crosslinked with itself and the fully cured composition has a storage modulus value of at least 175,000 Pa at 20° C., a shear adhesion failure temperature of at least 425° F. (218.3° C.) at 1 Kg/in$^2$ (0.155 Kg/cm$^2$), a heated shear value at 160° C. of greater than 10,000 minutes and a peel force value of at least 3.2 lb./in.

13. The composition as defined in claim 12 wherein the fully cured composition has a tan delta value of less than 0.8 as measured at 20° C. after the second curing stage.

14. The composition as defined in claim 12 wherein the fully cured composition has a room temperature shear adhesion value of least 200 hours at 10 lb./in$^2$ (4.5 Kg/cm$^2$) after the second curing stage.

15. The composition as defined in claim 12 wherein the fully cured composition has a visible light transmission of between 80 to 100%.

16. A partially cured adhesive composition comprising:
(a) a benzophenone-functionalized crosslinked acrylic copolymer;
(b) a multi-functionalized crosslinkable oligomer comprising a functional moiety selected from the group consisting of acrylate, epoxy, hydroxy, and combinations thereof;
(c) a photoinitiator which initiates polymerization of the oligomer; and
wherein the composition is free of a mono-functionalized oligomer; the acrylic copolymer is crosslinked with itself; and the partially cured composition has a tan δ value greater than 0.6 as measured at 20° C.

17. A partially cured adhesive composition as defined in claim 16, wherein said oligomer is adapted for crosslinking with itself by a radiation curing stage to produce a fully cured composition having a storage modulus value of at least 175,000 Pa at 20° C., a shear adhesion failure temperature of at least 425° F. (218.3° C.) at 1 Kg/in$^2$ (0.155 Kg/cm$^2$), a heated shear value at 160° C. of greater than 10,000 minutes and a peel force value of at least 3.2 lb./in.

18. A partially cured adhesive composition as defined in claim 16, wherein the acrylic copolymer is a solvent-free benzophenone-functionalized acrylic copolymer.

19. A partially cured adhesive composition as defined in claim 16, wherein the acrylic copolymer is polymerized from 2-ethylhexyl acrylate or butyl acrylate.

20. A partially cured adhesive composition as defined in claim 16, wherein the acrylic copolymer is crosslinked by exposure to light having a wavelength substantially less than 300 nm.

21. A partially cured adhesive composition as defined in claim 16, wherein the oligomer comprises a urethane oligomer having an acrylate functional moiety.

22. A partially cured adhesive composition as defined in claim 16, wherein the oligomer is present in an amount of at least 10% by weight relative to the dry weight of the acrylic copolymer.

23. A partially cured adhesive composition as defined in claim 16, wherein the photoinitiator is present in an amount of between 0.5 to 5% by weight relative to the dry weight of the acrylic copolymer.

24. A partially cured adhesive composition as defined in claim 16, wherein the photoinitiator is selected from the group consisting of acetophenone, aryl phosphineoxides, aryl sulfonium and aryl iodonium salts of hexafluorophophate, benzyl/benzoin, benzophenone, thioxanthone, and combination thereof.

25. A method for making an adhesive composition comprising:
(i) crosslinking an acrylic copolymer with itself in a first curing stage in the presence of
(a) a multi-functionalized oligomer having a functional moiety selected from the group of acrylate, epoxy, hydroxy, and combinations thereof; and
(b) a photoinitiator adapted for irradiative polymerization of the oligomer;
to produce a partially cured composition having a tan δ value greater than 0.6 as measured at 20° C., wherein the composition is free of a mono-functionalized oligomer.

26. A method for making an adhesive composition, as defined in claim 25, further comprising an additional step of:
(ii) crosslinking the oligomer with itself in the partially cured composition of step (i) in a second sequential radiation curing stage to produce a fully cured composition having a storage modulus value of at least 175,000 Pa at 20° C., a shear adhesion failure temperature of at least 425° F. (218.3° C.) at 1 Kg/in$^2$ (0.155 Kg/cm$^2$), a heated shear value at 160° C. of greater than 10,000 minutes and a peel force value of at least 3.2 lb./in.

27. A method for making an adhesive composition, as defined in claim 25, wherein said acrylic copolymer is benzophenone-functionalized.

28. A method for making an adhesive composition, as defined in claim 25, wherein the acrylic copolymer is a solvent-free benzophenone-functionalized acrylic copolymer.

29. A method for making an adhesive composition, as defined in claim 25, wherein the acrylic copolymer is polymerized from 2-ethylhexyl acrylate or butyl acrylate.

30. A method for making an adhesive composition, as defined in claim 25, wherein the acrylic copolymer is crosslinked during the first curing stage by exposure to light having a wavelength less than 300 nm.

31. A method for making an adhesive composition, as defined in claim 25, wherein the oligomer comprises a urethane oligomer having an acrylate functional moiety.

32. A method for making an adhesive composition, as defined in claim 25, wherein the oligomer is present in an amount of at least 10% by weight relative to the dry weight of the acrylic copolymer.

33. A method for making an adhesive composition, as defined in claim 25, wherein in the photoinitiator is present in an amount of between 0.5 to 5% by weight relative to the dry weight of the acrylic copolymer.

34. A method for making an adhesive composition, as defined in claim 26, wherein the oligomer is crosslinked during the second curing stage by exposure to light having a wavelength greater than 300 nm.

35. A method for making an adhesive composition, as defined in claim 26, wherein the oligomer is crosslinked during the second curing stage by exposure to light having a wavelength of between 320 to 440 nm.

36. A method for making an adhesive composition, as defined in claim 26, wherein the fully cured composition has a tan delta value of less than 0.8 as measured at 20° C.

37. A method for making an adhesive composition, as defined in claim 26, wherein the fully cured composition has a room temperature shear adhesion value of least 200 hours at 10 lb./in$^2$ (4.5 Kg/cm$^2$).

38. A method for making an adhesive composition, as defined in claim 25, wherein the photoinitiator is selected from the group consisting of acetophenone, aryl phosphineoxides, aryl sulfonium and aryl iodonium salts of hexafluorophophate, benzyl/benzoin, benzophenone, thioxanthone, and combination thereof.

39. A method for making an adhesive composition, as defined in claim 26, wherein the fully cured composition has a visible light transmission of between 80 to 100%.

\* \* \* \* \*